United States Patent
Kecskemethy et al.

(10) Patent No.: US 11,593,943 B2
(45) Date of Patent: Feb. 28, 2023

(54) RECIST ASSESSMENT OF TUMOUR PROGRESSION

(71) Applicant: KHEIRON MEDICAL TECHNOLOGIES LTD, London (GB)

(72) Inventors: Peter Kecskemethy, London (GB); Tobias Rijken, London (GB); Edith Karpati, Budapest (HU)

(73) Assignee: KHEIRON MEDICAL TECHNOLOGIES LTD, London (GB)

( * ) Notice: Subject to any disclaimer, the term of this patent is extended or adjusted under 35 U.S.C. 154(b) by 657 days.

(21) Appl. No.: 16/604,656

(22) PCT Filed: Apr. 11, 2018

(86) PCT No.: PCT/GB2018/050969
§ 371 (c)(1),
(2) Date: Oct. 11, 2019

(87) PCT Pub. No.: WO2018/189541
PCT Pub. Date: Oct. 18, 2018

(65) Prior Publication Data
US 2020/0074634 A1 Mar. 5, 2020

(30) Foreign Application Priority Data
Apr. 11, 2017 (GB) .................................. 1705876

(51) Int. Cl.
*G06T 7/00* (2017.01)
*G06T 7/62* (2017.01)
(Continued)

(52) U.S. Cl.
CPC .......... *G06T 7/0016* (2013.01); *A61B 5/0035* (2013.01); *A61B 5/015* (2013.01);
(Continued)

(58) Field of Classification Search
CPC ......... G06T 2207/10081; G06T 7/0012; G06T 2207/10088; G06T 2207/30096;
(Continued)

(56) References Cited

U.S. PATENT DOCUMENTS 6,075,879 A 6/2000 Roehrig et al.
6,324,532 B1 11/2001 Spence et al.
(Continued)

FOREIGN PATENT DOCUMENTS

CN 105931226 A 9/2016
CN 106096491 A 11/2016
(Continued)

OTHER PUBLICATIONS

Sun, et al., "Enhancing deep convolutional neural network scheme for breast cancer diagnosis with unlabeled data," ELSEVIER—Computerized Medical Imaging and Graphics 57 (2017). 6 pages.
(Continued)

*Primary Examiner* — Alex Kok S Liew
(74) *Attorney, Agent, or Firm* — Finch & Maloney PLLC

(57) ABSTRACT

The present invention relates to a method and system that automatically finds, segments and measures lesions in medical images following the Response Evaluation Criteria In Solid Tumours (RECIST) protocol. More particularly, the present invention produces an augmented version of an input computed tomography (CT) scan with an added image mask for the segmentations, 3D volumetric masks and models, measurements in 2D and 3D and statistical change analyses across scans taken at different time points.

According to a first aspect, there is provided a method for determining volumetric properties of one or more lesions in medical images comprising the following steps: receiving image data; determining one or more locations of one or more lesions in the image data; creating an image segmen-
(Continued)

tation (i.e. mask or contour) comprising the determined one or more locations of the one or more lesions in the image data and using the image segmentation to determine a volumetric property of the lesion.

20 Claims, 2 Drawing Sheets

(51) Int. Cl.
| | |
|---|---|
| *G06T 7/11* | (2017.01) |
| *G06T 7/73* | (2017.01) |
| *G16H 30/20* | (2018.01) |
| *G16H 50/20* | (2018.01) |
| *A61B 5/00* | (2006.01) |
| *A61B 5/01* | (2006.01) |
| *A61B 5/107* | (2006.01) |
| *A61B 6/03* | (2006.01) |
| *G06K 9/62* | (2022.01) |
| *G06N 3/04* | (2023.01) |
| *G06N 3/084* | (2023.01) |

(52) U.S. Cl.
CPC .......... *A61B 5/1073* (2013.01); *A61B 5/4842* (2013.01); *A61B 5/4887* (2013.01); *A61B 5/7267* (2013.01); *A61B 6/032* (2013.01); *G06K 9/628* (2013.01); *G06K 9/6228* (2013.01); *G06N 3/04* (2013.01); *G06N 3/084* (2013.01); *G06T 7/11* (2017.01); *G06T 7/62* (2017.01); *G06T 7/73* (2017.01); *G16H 30/20* (2018.01); *G16H 50/20* (2018.01); *G06T 2207/10081* (2013.01); *G06T 2207/20076* (2013.01); *G06T 2207/20081* (2013.01); *G06T 2207/20084* (2013.01); *G06T 2207/30096* (2013.01); *G06V 2201/03* (2022.01)

(58) Field of Classification Search
CPC . G06T 7/11; G06T 2207/30016; G06T 7/149; G06T 2200/24; G06T 7/12; G06T 2210/41; G06T 2207/20081; G06T 2207/20084; G06T 2207/30056; G06T 2200/04; G06T 2207/10072; G06T 7/0014; G06T 19/20; G06T 2207/20116; G06T 2207/30068; G06T 2207/20101; G06T 2207/30064; G06T 2219/028; G06T 7/30; G06T 11/003; G06T 17/00; G06T 2207/10136; G06T 2207/10132; G06T 7/187; G16H 30/40; G16H 50/20; G16H 30/20; G16H 40/20; G16H 50/30
See application file for complete search history.

(56) References Cited

U.S. PATENT DOCUMENTS

| | | | |
|---|---|---|---|
| 6,463,425 | B2 | 10/2002 | Raz |
| 9,589,374 | B1 | 3/2017 | Gao et al. |
| 10,127,659 | B2 | 11/2018 | Hsieh et al. |
| 11,127,137 | B2 | 9/2021 | Heindl et al. |
| 2005/0113651 | A1 | 5/2005 | Wood et al. |
| 2006/0050958 | A1* | 3/2006 | Okada ............... G06T 7/11 382/173 |
| 2006/0274928 | A1 | 12/2006 | Collins et al. |
| 2007/0003119 | A1 | 1/2007 | Roehrig et al. |
| 2011/0123087 | A1 | 5/2011 | Nie et al. |
| 2011/0150313 | A1 | 6/2011 | Su et al. |
| 2013/0343626 | A1 | 12/2013 | Rico et al. |
| 2014/0355840 | A1 | 12/2014 | Peyton |
| 2016/0350946 | A1 | 12/2016 | Schieke et al. |
| 2017/0039412 | A1* | 2/2017 | Solanki ............... G06T 7/0014 |
| 2018/0061054 | A1 | 3/2018 | Abraham et al. |
| 2018/0129900 | A1 | 5/2018 | Kiraly et al. |
| 2018/0165809 | A1 | 6/2018 | Stanitsas et al. |
| 2018/0218495 | A1 | 8/2018 | Ben-Ari |
| 2018/0218497 | A1 | 8/2018 | Golden et al. |
| 2020/0074632 | A1 | 3/2020 | Heindl et al. |
| 2020/0167928 | A1 | 5/2020 | Heindl et al. |
| 2020/0342589 | A1 | 10/2020 | Heindl et al. |

FOREIGN PATENT DOCUMENTS

| | | |
|---|---|---|
| CN | 106204587 A | 12/2016 |
| JP | 2006255412 A | 9/2006 |
| JP | 2008541889 A | 11/2008 |
| JP | 2016534709 A | 11/2016 |
| WO | 2008050332 A2 | 5/2008 |
| WO | 2008088478 A1 | 7/2008 |
| WO | 2015031641 A1 | 3/2015 |
| WO | 2015077076 A1 | 5/2015 |
| WO | 2017210690 A1 | 12/2017 |
| WO | 2018189541 A1 | 10/2018 |
| WO | 2018189549 A1 | 10/2018 |
| WO | 2018189550 A1 | 10/2018 |
| WO | 2018189551 A1 | 10/2018 |

OTHER PUBLICATIONS

Long, et al., "Fully Convolutional Networks for Semantic Segmentation," Proc. of IEEE Computer Vision and Pattern Recognition, 201, 3431-3440, https://openaccess.thecvf.com/content_cvpr_2015/papers/Long_Fully_Convolutional_Networks_2015_CVPR_paper.pdf.
JP Office Action issued for JP2020-505539, dated Mar. 8, 2022, 5 pages. (including English translation).
International Search Report and Written Opinion received for Patent Application No. PCT/GB2018/050969, dated Jun. 26, 2018. 20 pages.
International Preliminary Report on Patentability received for Patent Application No. PCT/GB2018/050969, dated Oct. 15, 2019. 12 pages.
International Search Report and Written Opinion received for PCT Application No. PCT/GB2018/050980, dated Jul. 12, 2018. 34 pages.
International Preliminary Report on Patentability received for PCT Application No. PCT/GB2018/050980, dated Oct. 15, 2019. 11 pages.
Combined Search and Examination Report under Sections 17 and 18(3) received for GB Application No. 1711558.5, dated Dec. 22, 2017. 6 pages.
International Search Report and Written Opinion received for Patent Application No. PCT/GB2018/050979, dated Jul. 9, 2018. 36 pages.
International Preliminary Report on Patentability received for Patent Application No. PCT/GB2018/050979, dated Oct. 15, 2019. 11 pages.
Combined Search and Examination Report under Sections 17 and 18(3) received for GB Application No. 1711557.7, dated Jan. 18, 2018. 5 pages.
International Search Report and Written Opinion received for Patent Application No. PCT/GB2018/050981, dated Jul. 9, 2018. 23 pages.
International Preliminary Report on Patentability received for Patent Application No. PCT/GB2018/050981, dated Oct. 15, 2019. 15 pages.
Combined Search and Examination Report under Sections 17 and 18(3) received for GB Application No. 1711559.3 dated Dec. 19, 2017. 7 pages.
Christ, et al., "Automatic Liver and Tumor Segmentation of CT and MRI Volumes Using Cascaded Fully Convolutional Neural Networks," arXiv: 1702.05970v2 [cs.CV], Feb. 23, 2017. 20 pages.
Christ, et al., "Survivalnet: Predicting Patient Survival From Diffusion Weighted Magnetic Resonance Images Using Cascaded Fully Convolutional and 3D Convolutional Neural Networks," arXiv: 1702.05941v1 [cs.CV], Feb. 20, 2017. 6 pages.

(56) References Cited

OTHER PUBLICATIONS

Hou, et al., "Patch-based Convolutional Neural Network for Whole Slide Tissue Image Classification," IEEE Conference On Computer Vision and Pattern Recognition, (CVPR) Jun. 27, 2016. pp. 2424-2433.

Menechelli, et al., "Automatic breast tissue density estimation scheme in digital mammography images," Progress in Biomedical Optics and Imaging, SPIE—International Society for Optical Engineering., vol. 10136, Mar. 10, 2017. 12 pages.

Ronneberger, et al., "U-Net: Convolutional Networks for Biomedical Image Segmentation," Medical Image Computing and Computer-Assisted Intervention—MICCAI 2015—18th International Conference. Nov. 18, 2015, Springer International Publishing, arXiv: 1505.04597v1, May 18, 2015. 8 pages.

Yu, et al., "Automated Melanoma Recognition in Dermoscopy Images via Very Deep Residual Networks," IEEE Transactions On Medical Imaging. Dec. 2016. 12 pages.

El Hamdi, et al., "Breast Cancer Diagnosis Using a Hybrid Evolutionary Neural Network Classifier," 18th Mediterranean Conference on Control & Automation, Jun. 23-25, 2010, pp. 1308-1315.

Communication pursuant to Article 94(3) EPC received for EP Application No. 18719273.7, dated Nov. 11, 2021. 9 pages.

JP Office Action received for JP Application No. 2020-505540, dated Apr. 19, 2022. 3 pages.

Akselrod-Ballin, et al., "A Region Based Convolutional Network for Tumor Detection and Classification in Breast Mammography," Springer International Publishing AG, 2016, G. Carneiro et al. (Eds): LABELS 2016/DLMIA 2016, LNCS 10008, pp. 197-205.

Gram, et al., "The Tabar classification of mammographic parenchymal patterns," ELSEVIER, European Journal of Radiology 24 (1997), pp. 131-136.

Kallenberg, et al., "Unsupervised Deep Learning Applied to Breast Density Segmentation and Mammographic Risk Scoring," IEEE Transactions on Medical Imaging, vol. 35, No. 5, May 2016. pp. 1322-1331.

Winkel, et al., "Mammographic density and structural features can individually and jointly contribute to breast cancer risk assessment in mammography screening: a case-control study," BMC Cancer (2016) DOI 10.1186/s 12885-016-2450-7. pp. 1-12.

Communication pursuant to Article 94(3) EPC received for EP Application No. 18719271.1, dated Jun. 21, 2021. 10 pages.

Communication pursuant to Article 94(3) EPC received for EP Application No. 18719272.9, dated Jun. 21, 2021. 8 pages.

\* cited by examiner

RECIST ASSESSMENT OF TUMOUR PROGRESSION

FIELD OF THE INVENTION

The present invention relates to a method and system that automatically finds, segments and measures lesions in medical images following the Response Evaluation Criteria In Solid Tumours (RECIST) protocol. More particularly, the present invention produces an augmented version of an input computed tomography (CT) scan with an added image mask for the segmentations, 3D volumetric masks and models, measurements in 2D and 3D and statistical change analyses across scans taken at different time points.

BACKGROUND TO THE INVENTION

CT scans make use of x-ray imaging from a number of different angles to produce cross sectional slices of a scanned patient. Although CT scans provide radiologists a useful tool to identify, locate and classify lesions in patients, it is difficult to perform volumetric measurements of lesions from CT images in acceptable amount of time due to the sheer number of image slices contained in each CT scan.

CT scans are usually presented in grayscale and therefore consist of only one colour channel. This creates problems when radiologists want to view different elements of the image as the human eye is capable of distinguishing a limited number of grey levels that are not sufficient to visualise all the information in a CT slice. The different elements are presented in varying brightness-contrast settings on a number of different windows. For example, the view of skeletal element of the scan may be best viewed in one brightness-contrast setting (called 'window'), the view of the organs in another window, etc. Radiologists therefore have to look at different contrast windows in order to identify and locate lesions. It is an aim of the present invention to provide a solution to this problem.

Medical imaging devices usually encapsulate the scans into the Digital Imaging and Communications in Medicine (DICOM) format to enable more efficient handling, storing, printing and transmitting of medical imaging information.

The RECIST protocol is a set of rules that are used to assess the behaviour of a tumour in a patient. The RECIST protocol also provides a method that can be used to measure lesions, however, the current method requires a vast amount of input and uninformed decisions made before treatment from the radiologists which may result in inaccurate measurements, the inability to record measurements on suspect tumours and more importantly not identifying a lesion from an image.

When assessing tumour progression, radiologists need to assess tumour burden for scans performed at different time points and compare the results. It is critical that the same lesions are accurately identified at different time points and assessed for the purpose of comparison. The co-location and comparison process is a burdensome and inherently inaccurate.

When assessing tumour burden, radiologists perform 1D measurements of portions of lesions that fall into the 2D slices produced. This measurement is inherently limited in how accurately it represents tumour burden provided by a single lesion.

SUMMARY OF THE INVENTION

Aspects and/or embodiments seek to provide a method of automatically locating and measuring lesions/tumours/ growths and tumour changes in medical images. Aspects and/or embodiments also seek to address the problem relating to human error inaccuracy by performing identification, measurement and statistical analysis steps automatically.

According to a first aspect, there is provided a method for determining volumetric properties of one or more lesions in medical images comprising the following steps: receiving image data; determining one or more locations of one or more lesions in the image data; creating an image segmentation (i.e. mask or contour) comprising the determined one or more locations of the one or more lesions in the image data and using the image segmentation to determine a volumetric property of the lesion.

In this way, automatic detection and localisation of one or more lesions can be performed using the image data. It can also automatically provide properties (e.g. classification, volume, shape, size) relating to one or more lesions without needing any human intervention. A segmentation (i.e. mask or contour) is also created in order to allow the location of one or more lesions to be easily observed. Unlike current methods, this enables volumetric assessment of medical image more accurately over a period of time which is indicative of whether a tumour is progressing or regressing.

Optionally, the step of determining one or more locations of the one or more lesions comprises identifying a focal point of the one or more lesions. Optionally, the focal point of the one or more lesions comprises a centre of mass for the one or more lesions.

Optionally, the step of determining one or more locations of the one or more lesions comprises identifying a focal point of the one or more anatomical landmarks. Optionally, the focal point of the one or more anatomical landmarks comprises a centre of mass for the one or more lesions.

By using a focal point such as a centre of mass for the lesion or anatomical region, the assessment of the locations will be consistent throughout scans and between scans where scans are taken at iterative time intervals of the same patient. For example, although the tumour may grow the centre of mass will always remain substantially constant thus the same tumour can be identified in the same patient in different scans of the same portion of that patient's anatomy.

Optionally, the step of determining one or more locations of the one or more lesions comprises determining the location relative to one or more anatomical landmarks. Optionally, the one or more anatomical landmarks comprise any one of: spine, ribs, lungs, and heart, liver, kidneys.

Optionally, the step of determining one or more locations of the one or more lesions comprises identifying a focal point of the one or more lesions, identifying a focal point of the one or more anatomical landmarks and determining the location of the one or more lesions relative to one or more anatomical landmarks. In this way, a tumour can be localised relative to other anatomical objects.

By identifying landmarks, the relative position of landmarks to any tumours can be established and used as a way to identify the same tumour between scans, for example where the scans are taken at iterative time intervals.

Optionally, the image data comprises any one of or any combination of: CT scan data; DICOM image files; a sequence of images of sequential slices of anatomy; one or more grayscale images; demographic patient information; prior imaging data.

Optionally, the image data comprises one or more images, optionally wherein the one or images relate to a common portion of a common patient anatomy.

Optionally, the one or more images are captured at different times. Optionally, the one or more images comprise a plurality of 2D slices of a 3D representation. Although the initial scan is a 3D representation of the patient, the method is applied to 2D slices of the initial 3D scan.

Optionally, the step of segmenting the one or more lesions to create lesion segmentation data; and storing the lesion segmentation data in the image mask/contour.

Optionally, the image segmentation comprises creating a mask or contour. The segmentation masks can be combined to create a 3D representation of the tumour.

Optionally, the step of measuring the one or more lesions to create lesion measurement data; and storing the lesion segmentation and measurement data in connection with the image mask.

Optionally, the step of pre-processing the image data, wherein pre-processing comprises reading the image data and storing the image data in a memory.

Optionally, the image data is stored in memory as at least a four-dimensional tensor wherein the dimensions comprise: height, width, batch size and channels.

Optionally, the channels comprise one or more contrast windows or contrast values.

Optionally, the step of determining one or more locations of the one or more lesions in the image data comprises using a convolutional neural network.

Optionally, the step of determining one or more locations of the one or more lesions in the image data comprises using a fully convolutional neural network.

Optionally, the full convolutional neural network is trained using backpropagation; and/or the loss function for dense training is the sum over the spatial dimensions of the loss functions of the individual pixels.

Optionally, the method further comprises creating one or more heat maps to indicate areas within respective one or more images of the image data having a high probability of being a tumour.

Optionally, the method further comprises the step of post-processing the one or more heat maps by feeding the one or more heat maps through a conditional random field method.

Optionally, the method further comprises the step of post-processing the determined one or more locations of the one or more lesions in the image data by feeding the determined one or more locations through a conditional random field method.

According to a second aspect, there is provided an apparatus operable to perform the method of any preceding claim.

According to a third aspect, there is provided a system comprising the apparatus of the preceding claim.

A further aspect relates to a computer program product operable to perform the method of any preceding claim.

SPECIFIC DESCRIPTION

Figure 1:
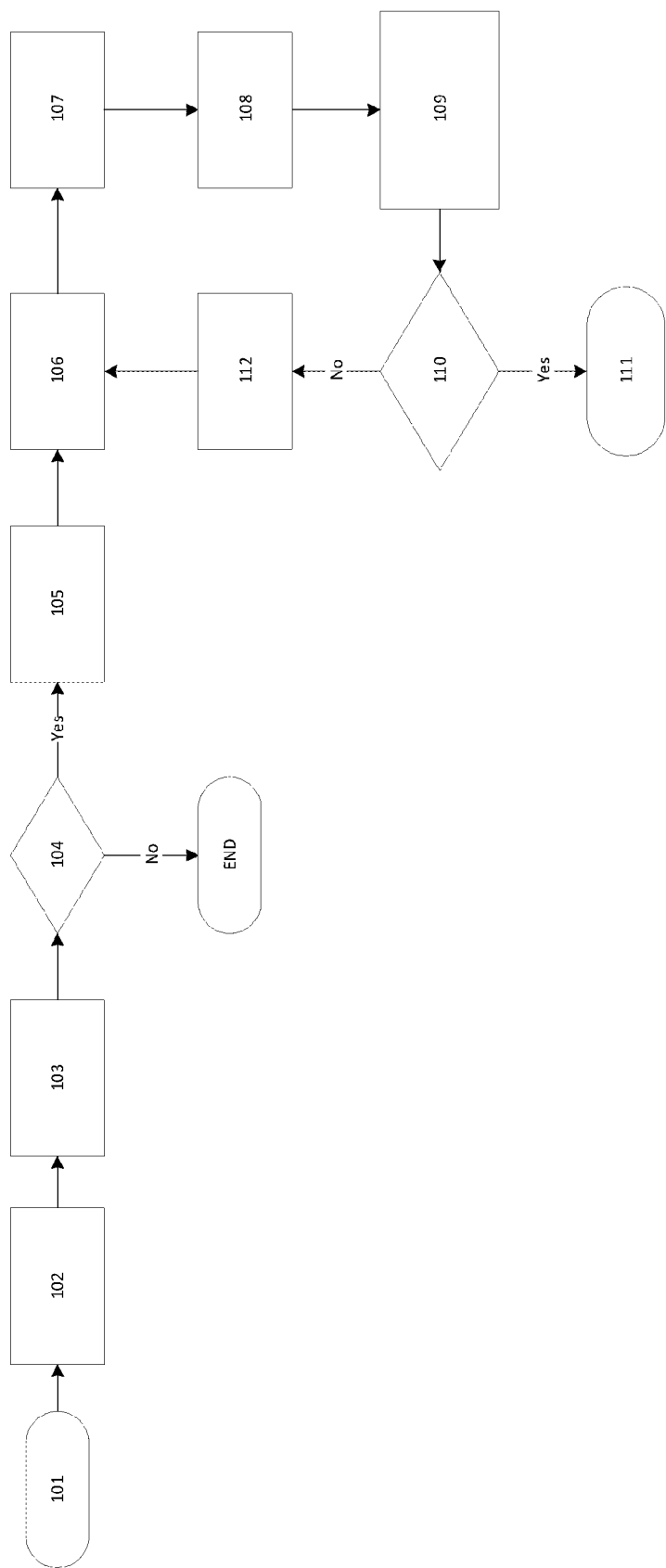
FIG. 1 illustrates a flowchart showing the methods of existing RECIST systems.

FIG. 1 depicts the method of current manual RECIST systems. As seen in the flowchart, having performed a medical scan (CT, MRI, X-Ray) of a patient 101, the scanned images are collated in a DICOM format 102.

As previously mentioned, elements corresponding to different contrasts are displayed in windows. From this information, following the manual process a radiologist would select between 4 to 8 tumours 103 to analyse before proceeding to select an appropriate method of treatment.

In accordance with the RECIST protocols the lesion (or tumour) must be measurable. Therefore, once the tumours are selected, a determination is made as to whether or not the tumours can be measured by the radiologist. If they can, the measurements are recorded across one dimension by the radiologist 105. Since the information presented to the radiologist will be limited to the two-dimensional display of a screen, the measurements can only be across one dimension.

These measurements are then used to determine the treatment method 106.

After performing a treatment on the tumour a follow-up medical scan is performed 107. The system seeks to identify the previously identified tumours from the new follow-up scans by repeating the aforementioned steps 108.

If the previously identified tumour is found, using the new follow-up scan, the radiologist measures the tumour once more 109. Upon recording the measurements for the follow-up scan, they are compared to the measurements of the tumour in the previous scan to determine whether the tumour size has changed 110.

At this point, if the tumour has decreased in size, the system will advise the radiologist to proceed with the same course of treatment until the patient is cured 111. However, if the tumour size has not decreased, the system will advise pursuing an alternative treatment method 112. The loop of this treatment phase will continue until the patient is cured.

An example embodiment will now be described in reference to FIG. 2, wherein a typical implementation of the method according to at least one embodiment is shown.

Figure 2:
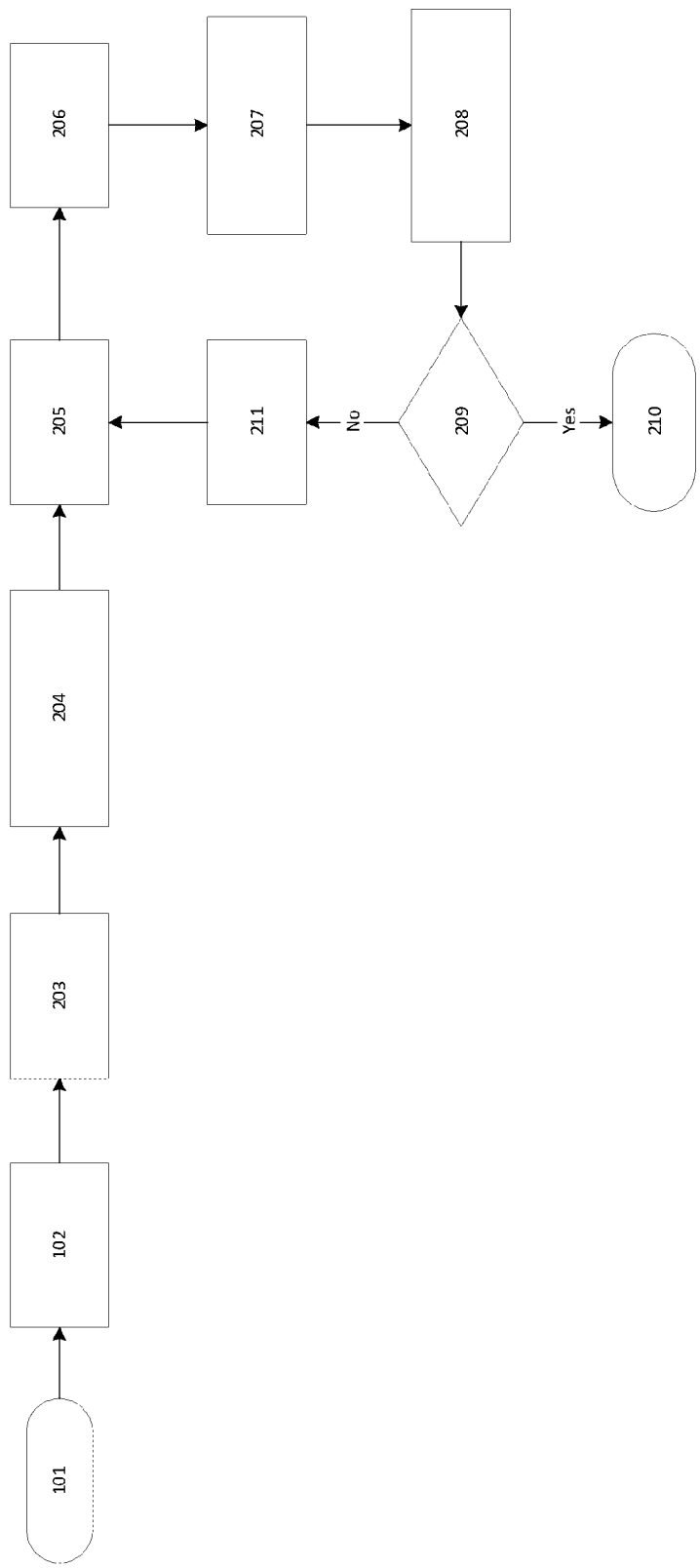
FIG. 2 illustrates a flowchart showing the methods of the present invention.

In FIG. 2, a pre-processing module 203 reads the DICOM files and loads 2D image slices into the system. The image slices are loaded into a 4-dimensional tensor of size [batch size, height, width, channels].

Measurements can be digitally analysed and recorded across one or more dimensions, and/or measurements can be performed volumetrically 204.

The images may be gathered at time intervals from the same patient and each time a new scan is performed for the patient the process of the embodiment is carried out with both the historical data and the new data to assess the changes between observations, as discussed later.

Once the DICOM image has been processed the different contrast channels corresponding to different elements of the patient scan are presented in the same window. This allows the system to look at all the elements at the same time. As an example, by applying different windowing levels to the images and feeding these as separate input channels, the patient's bones can be easily segmented from the scan.

Further context can be given to the model by adding the preceding and subsequent slices in the imaging sequence as additional channels in the input tensor. In this scenario, the input tensor would have three channels, where the first channel is the previous slice, the second channel is the "current" slice, which corresponds to the associated target mask, and the third channel is the subsequent slice. For example, as mentioned above, with the input tensor being a 4D tensor, [batch size, height, width, channels], the channel value would be "3", and the corresponding mask to this input is a 4D tensor, [batch size, height, width, channels], where the channel value is "1". The mask is the corresponding target for the "current" slice in channel 2.

The image tensor is fed into a Fully Convolutional Network (FCN) which creates a heat map indicating areas where there is a high probability of the existence of a tumour. These lesions are then segmented. Additionally, the segmentations are post-processed by feeding it through a Conditional Random Field, which "cleans up" the segmentation, i.e. remove false positives. The heat maps created by the FCN represent a probability map for the image.

The FCN is trained using backpropagation and forward pass through the network. The loss function for dense training is the sum over spatial dimensions of the loss functions of the individual pixels.

$$L(x) = \sum_{i,j} l'(x_{i,j})$$

here $L(x)$ is the loss over the whole image and $l'(x_{i,j})$ is the loss for the pixel at i,j. This enables the system to automatically identify one or more tumours from the image created by the system.

The loss function may be the DICE loss, which is defined as $$L_{DSC} = \frac{2\sum_i^N s_i r_i}{\sum_i^N s_i + \sum_i^N r_i}$$

where $s_i$ and $r_i$ represent the continuous values of the prediction map $\in[0, \ldots, 1]$ and the ground truth at each pixel i, respectively. Alternatively, a cross-entropy can be used. The cross-entropy loss for the pixel at i,j is defined as $$L_{CE} = -\sum_{c=1}^c y * \log(s)$$

where C is the number of classes, $y \in \{0,1\}$ is the binary indicator for class c, and s is the score for class c. The loss for the full image, x, is defined as the sum over all the losses for the pixels:

$$L_{CE}(x) = \sum_{i,j}\left(-\sum_{c=1}^C y * \log(s)\right)$$

After the model has been trained, lesions may be segmented by feeding an image to the model. The resulting output will be a probability map, which can be thresholded to obtain a segmentation mask or contour.

In order to identify the same lesions in a patient across different scans, the system uses landmarks to construct a representation for the location of a lesion relative to the landmarks. These representations can be compared across and examinations or scans. In this way, a lesion can be found in a different scan even when other characteristics of the lesion (e.g. size and shape) have changed.

A lesion's location representation can be defined as a vector $h \in R^L$, where R is the set of positive real numbers, and L is the number of landmarks. For example, a location representation for a specific lesion could be $h_i$=[0.43, 0.2, 0.98, 1.3]. Each element in the location representation is the (Euclidian) distance between a focal point of the lesion, such as the centre of mass of the lesion, and a focal point of landmark, such as the centre of mass of the landmark. The centre of mass of a lesion and/or landmark is defined as follows:

$$R = \frac{1}{n}\sum_{i=1}^n r_i$$

where n is the number of pixels in the volume (i.e. lesion or landmark), $r_i$ is the coordinate vector for pixel i, and R is the coordinate vector for the centre of mass. The Euclidian distance between the centre of mass of the lesion, p, and the landmark, q, is then:

$$d(p, q) = \sqrt{\sum_i^n (p_i - q_o)^2}$$

The location representation vectors for two lesions across two different exams can be compared using a similarity metric such as the cosine distance or the Euclidian distance. When the distance is small, the lesions can be said to be the same.

With the system having identified and segmented the tumours, measurements of the or each tumour are digitally analysed and recorded across one or more dimensions before proceeding to a treatment phase 204. This should substantially eliminate the possibilities of human error and inaccuracy, therefore increasing the likelihood of every tumour or growth to be measured. In some cases, an appropriate treatment plan/dose can then be administered to the tumour 205.

After an iteration of time, a follow-up medical scan is performed 206. The system seeks to identify the previously identified tumours from the new follow-up scans by carrying out the previously mentioned steps 207. In addition, the system also identifies any additional growths that may have developed in the new follow-up scan. The relative positions of previous landmarks, in particular the centre of mass of each landmark, is used to identify the same growths between scans.

If any tumours/growths are identified in the follow-up scan, the measurements are again digitally analysed and recorded across one or more dimensions 208. Once measurements for the follow-up scan are recorded, they are compared to the measurements of the tumour/growth in the previous scan to determine whether the tumour size has changed 209. The size of the tumour that is being compared is the volume of the or each tumour between scans.

Similar to FIG. 1, if the tumour has decreased in size, the system will proceed with the same course of treatment until the patient is cured 210. However, if the tumour size has not decreased, the system will pursue an alternative treatment method before administering the new treatment 211. The loop of the treatment phase will continue until the patient is cured.

Machine learning is the field of study where a computer or computers learn to perform classes of tasks using the feedback generated from the experience or data gathered that the machine learning process acquires during computer performance of those tasks.

Typically, machine learning can be broadly classed as supervised and unsupervised approaches, although there are particular approaches such as reinforcement learning and semi-supervised learning which have special rules, techniques and/or approaches. Supervised machine learning is concerned with a computer learning one or more rules or functions to map between example inputs and desired outputs as predetermined by an operator or programmer, usually where a data set containing the inputs is labelled.

Unsupervised learning is concerned with determining a structure for input data, for example when performing pattern recognition, and typically uses unlabelled data sets. Reinforcement learning is concerned with enabling a computer or computers to interact with a dynamic environment, for example when playing a game or driving a vehicle.

Various hybrids of these categories are possible, such as "semi-supervised" machine learning where a training data set has only been partially labelled. For unsupervised machine learning, there is a range of possible applications such as, for example, the application of computer vision techniques to image processing or video enhancement. Unsupervised machine learning is typically applied to solve problems where an unknown data structure might be present in the data. As the data is unlabelled, the machine learning process is required to operate to identify implicit relationships between the data for example by deriving a clustering metric based on internally derived information. For example, an unsupervised learning technique can be used to reduce the dimensionality of a data set and attempt to identify and model relationships between clusters in the data set, and can for example generate measures of cluster membership or identify hubs or nodes in or between clusters (for example using a technique referred to as weighted correlation network analysis, which can be applied to high-dimensional data sets, or using k-means clustering to cluster data by a measure of the Euclidean distance between each datum).

Semi-supervised learning is typically applied to solve problems where there is a partially labelled data set, for example where only a subset of the data is labelled. Semi-supervised machine learning makes use of externally provided labels and objective functions as well as any implicit data relationships. When initially configuring a machine learning system, particularly when using a supervised machine learning approach, the machine learning algorithm can be provided with some training data or a set of training examples, in which each example is typically a pair of an input signal/vector and a desired output value, label (or classification) or signal. The machine learning algorithm analyses the training data and produces a generalised function that can be used with unseen data sets to produce desired output values or signals for the unseen input vectors/signals. The user needs to decide what type of data is to be used as the training data, and to prepare a representative real-world set of data. The user must however take care to ensure that the training data contains enough information to accurately predict desired output values without providing too many features (which can result in too many dimensions being considered by the machine learning process during training, and could also mean that the machine learning process does not converge to good solutions for all or specific examples). The user must also determine the desired structure of the learned or generalised function, for example whether to use support vector machines or decision trees.

The use of unsupervised or semi-supervised machine learning approaches are sometimes used when labelled data is not readily available, or where the system generates new labelled data from unknown data given some initial seed labels.

Machine learning may be performed through the use of one or more of: a non-linear hierarchical algorithm; neural network; convolutional neural network; recurrent neural network; long short-term memory network; multi-dimensional convolutional network; a memory network; fully convolutional network or a gated recurrent network allows a flexible approach when generating the predicted block of visual data. The use of an algorithm with a memory unit such as a long short-term memory network (LSTM), a memory network or a gated recurrent network can keep the state of the predicted blocks from motion compensation processes performed on the same original input frame. The use of these networks can improve computational efficiency and also improve temporal consistency in the motion compensation process across a number of frames, as the algorithm maintains some sort of state or memory of the changes in motion. This can additionally result in a reduction of error rates.

Developing a machine learning system typically consists of two stages: (1) training and (2) production. During the training the parameters of the machine learning model are iteratively changed to optimise a particular learning objective, known as the objective function or the loss. Once the model is trained, it can be used in production, where the model takes in an input and produces an output using the trained parameters.

Any system feature as described herein may also be provided as a method feature, and vice versa. As used herein, means plus function features may be expressed alternatively in terms of their corresponding structure.

Any feature in one aspect may be applied to other aspects, in any appropriate combination. In particular, method aspects may be applied to system aspects, and vice versa. Furthermore, any, some and/or all features in one aspect can be applied to any, some and/or all features in any other aspect, in any appropriate combination.

It should also be appreciated that particular combinations of the various features described and defined in any aspects can be implemented and/or supplied and/or used independently.

The invention claimed is:

1. A method for determining volumetric properties of one or more lesions in medical images, the method comprising:
   receiving image data;
   determining one or more locations of the one or more lesions in the image data;
   creating an image segmentation comprising the determined one or more locations of the one or more lesions in the image data;
   using the image segmentation to determine a volumetric property of the lesion;
   creating one or more heat maps to indicate areas within respective one or more images of the image data having a high probability of being a tumour; and
   post-processing the one or more heat maps by feeding the one or more heat maps through a conditional random field method.

2. The method of claim 1 wherein determining one or more locations of the one or more lesions comprises one or both of:
   identifying a focal point of the one or more lesions; and/or
   identifying a focal point of one or more anatomical landmarks.

3. The method of claim 2 wherein the focal point of the one or more lesions comprises a centre of mass for the one or more lesions, and/or the focal point of the one or more anatomical landmarks comprises a centre of mass for the one or more lesions.

4. The method of claim 1 wherein determining one or more locations of the one or more lesions comprises determining the location relative to one or more anatomical landmarks.

5. The method of claim 4 wherein the one or more anatomical landmarks comprise any one of: spine, ribs, lungs, heart, liver and kidneys.

6. The method of claim 1 wherein determining one or more locations of the one or more lesions comprises:
identifying a focal point of the one or more lesions;
identifying a focal point of the one or more anatomical landmarks; and
determining the location of the one or more lesions relative to one or more anatomical landmarks.

7. The method of claim 1 wherein the image data comprises any one of or any combination of: CT scan data; a DICOM image file; a sequence of images of sequential slices of anatomy; one or more grayscale images; demographic patient information; prior imaging data; one or more images.

8. The method of claim 1 further comprising:
segmenting the one or more lesions to create lesion segmentation data; and
storing the lesion segmentation data in the image segmentation.

9. The method of claim 8 wherein the image segmentation comprises a mask or contour.

10. The method of claim 1 further comprising:
measuring the one or more lesions to create lesion measurement data; and
storing the lesion segmentation data in an image mask.

11. The method of claim 1 further comprising pre-processing the image data, wherein pre-processing comprises reading the image data and storing the image data in a memory, wherein the image data is stored in the memory as at least a four-dimensional floating-point tensor wherein the dimensions comprise: height, width, batch size, and channels, wherein the channels comprise one or more contrast windows and/or contrast values.

12. The method of claim 1 wherein determining one or more locations of the one or more lesions in the image data comprises using a fully convolutional neural network.

13. The method of claim 12 wherein the fully convolutional neural network is trained using backpropagation; and/or a loss function for dense training is the sum over the spatial dimensions of the loss functions of the individual pixels.

14. The method of claim 1 further comprising post-processing the determined one or more locations of the one or more lesions in the image data by feeding the determined one or more locations through a conditional random field method.

15. The method of claim 1 further comprising one or more of:
determining one dimensional measurements of found lesions, wherein the one-dimensional measurement comprises largest diameter or perpendicular diameter;
determining two-dimensional measurements of found lesions, optionally wherein the two-dimensional measurements comprises lesion area;
determining a three-dimensional model of found lesions with interpolation between 2D slices;
determining a largest diameter in three-dimensional space;
determining a volume and a surface in three-dimensional space;
determining the extent of necrosis with 1D and/or 2D and/or 3D measurements; and
determining disease stage based on any one of or any combination of lesion localizations, context variables, classifications, measurements, numbers and/or summary statistics of all these.

16. The method of claim 1 further comprising one or both of:
selecting target lesions according to a predetermined criteria, wherein the predetermined criteria comprises any one of or any combination of: malignancy, size, location, necrosis, other classification; and/or
selecting a number of target lesions based on a human-given or computer-given or computer-optimized probability threshold(s), yielding a number of trackable target lesions of potentially varying classes and/or varying locations and/or varying sizes.

17. The method of claim 1 further comprising locating and identifying the same lesion between scans taken at different time points using landmarks identified by computer and/or human.

18. The method of claim 1 wherein post-processing the one or more heat maps comprises removing one or more heat maps that indicate false positive tumour areas.

19. A system for determining volumetric properties of one or more lesions in medical images, the system:
a memory including instructions; and
one or more processors configured to execute the instructions to
receive image data;
determine one or more locations of the one or more lesions in the image data;
create an image segmentation comprising the determined one or more locations of the one or more lesions in the image data;
use the image segmentation to determine a volumetric property of the lesion;
create one or more heat maps to indicate areas within respective one or more images of the image data having a high probability of being a tumour; and
post-process the one or more heat maps by feeding the one or more heat maps through a conditional random field method.

20. A computer program product including one or more non-transitory machine readable mediums encoded with instructions that when executed by one or more processors cause a process to be carried out for determining volumetric properties of one or more lesions in medical images, the process comprising:
receiving image data;
determining one or more locations of the one or more lesions in the image data;
creating an image segmentation comprising the determined one or more locations of the one or more lesions in the image data;
using the image segmentation to determine a volumetric property of the lesion;
creating one or more heat maps to indicate areas within respective one or more images of the image data having a high probability of being a tumour; and
post-processing the one or more heat maps by feeding the one or more heat maps through a conditional random field method.

* * * * *